United States Patent [19]

Myrnes et al.

[11] Patent Number: 6,133,010

[45] Date of Patent: Oct. 17, 2000

[54] CHLAMYSIN B ANTIBACTERIAL PROTEIN, A PROTEIN GENE FOR AND AN EXPRESSION SYSTEM FOR SAME

[75] Inventors: Bjornar Myrnes; Inge Waller Nilsen; Kersti Overbo; Erling Sandsdalen, all of Tromso, Norway

[73] Assignee: Biotec ASA, Tromso, Norway

[21] Appl. No.: 09/349,884

[22] Filed: Jul. 8, 1999

[51] Int. Cl.[7] .............................. C12N 9/36; A61K 38/00

[52] U.S. Cl. ............................................ 435/206; 530/324

[58] Field of Search .............................. 530/350; 536/23.1

*Primary Examiner*—Ponnathapu Achutamurthy
*Assistant Examiner*—Christian L. Fronda
*Attorney, Agent, or Firm*—Ladas & Parry

[57] ABSTRACT

This invention relates to the novel antibacterial protein Chlamysin B, a novel protein gene encoding the Chlamysin B protein and an expression system using such gene in *E. Coli*.

5 Claims, No Drawings

CHLAMYSIN B ANTIBACTERIAL PROTEIN, A PROTEIN GENE FOR AND AN EXPRESSION SYSTEM FOR SAME

FIELD OF THE INVENTION

This invention relates to a novel antibacterial protein, a novel protein gene encoding the protein and a recombinant DNA process for the expression of the novel antibacterial protein.

BACKGROUND OF THE INVENTION

The wide-spread use of antibiotics over the past decades to treat infectious diseases in humans, farm animals and aquaculture species has led to a gradual selection of bacterial strains which are resistant to such medication. The problem with microbial resistance to antibiotics is of special concern for the human health sector, which for decades have had these powerful compounds to control diseases and prevent spreading of pathogenic bacteria in the environment. This situation has fostered an intensive search for new antibiotics which differ from those used today in mode of action and hence which are not affectd by the resistance genes, selected as a result of previous and present use of antibiotics. The search for novel antibacterial principles has included also the marine environment and invertebrates living in this environment. In recent years, antimicrobial substances have been isolated from marine invertebrates. This includes several antibacterial polypeptides from horseshoe crab, short crab and molluscs. These polypeptides exhibit an antibacterial activity against various Gram-positive and Gram-negative bacteria. Glycoproteins with antibacterial activity have been isolated from sea hare and a bivalve mollusc. One well-known antibacterial protein is lysozyme. Lysozyme, however, exhibits an antibacterial activity against extremely limited Gram-positive bacteria such as Micrococcus. It is well known that proteins with lysozyme-like activity occur in many marine invertebrates including marine bivalves. Such proteins are believed to be involved in the host defense as well as being associated with digestive processes in marine bivalves. Bacteria are nutritive sources for filter feeders such as marine bivalves and a substance that is able to hydrolyse bacteria would fulfill the purpose of both defense and digestion. While it is known that an extract from the viscera of the Arctic scallop has been shown to have antibacterial effects on *Aeromonas salmonicida* and *Vibrio salmonicida* in vitro, it is considered that the tedious process for the production of such extracts coupled with the volume of such extracts required to be of commercial significance precluded the use of such extracts as a commercial candidate for use in the killing of fish pathogens. Accordingly, if the lysozyme antibacterial component of the viscera of Arctic scallop could be isolated and identified and the gene be isolated therefrom which would permit then the expression of the lysozyme antibacterial protein, there could then be provided to the art a significant system for the production of a novel antibacterial protein in amounts that would render such antibacterial protein a real candidate for the inhibitation and killing of bacterial pathogens.

It is thus an object of the present invention to provide a novel isolated and characterized antibacterial protein which is derived from the Islandic scallop—*Chlamys islandica.*

Another object of this invention is to provide a novel, isolated and characterized gene protein which will express a novel lysozyme protein having antibacterial activity.

A still further object of this invention is to provide a process for the expression of a novel gene derived from the Islandic scallop *Chlamys islandica* in a host microbial system.

Yet another object of this invention is to provide a novel construct for the expression of an antibacterial lysozyme protein.

Other aspects, objects and the several advantages of this invention will be apparent from the following disclosure and appended claims.

SUMMARY OF THE INVENTION

In accordance with one embodiment of the present invention we have discovered a novel antibacterial protein Chlamysin B isolated from the viscera of the Islandic scallop which exhibits antibacterial activity against both Gram-positive and Gram-negative bacteria.

The isolated gene from the Icelandic scallop for Chlamysin B which represents another embodiment of this invention provides a gene useful in the formation of an expression vehicle whereby there is achieved the expression of Chlamysin B in a host organism.

DETAILED DESCRIPTION OF THE INVENTION

The novel protein of the present invention (hereinafter referred to as "Chlamysin B") can be obtained from the scallop waste of Arctic scallop (*Chlamys islandica*) through a process wherein scallop viscera is squeezed through a screw press. The flow through material (hereinafter referred to as "scallop viscera extract") is then collected. The scallop viscera extract is then clarified by hydrochloric acid precipitation. Following settling of the resulting flow, a brown supernatant is recovered. Chlamysin B present in the supernatant is then isolated by conventional methods for protein isolation. Chlamysin B is detected through the purification by measuring lysozyme activity at a pH of 5.2. The obtained supernatant is mixed with a buffer solution containing ammonium acetate and subjected to cation exchange column chromatography. Out of the fractions absorbed to the cation exchange column, the fractions that exhibit enzyme activity are pooled. The resulting pooled fraction is fractionated and concentrated using ultrafiltration. The pooled fraction is first concentrated using a membrane with a nominal molecular weight cut off of $10^5$ Dalton. Then the permeate obtained in this filtration is subsequently concentrated using a membrane with a nominal molecular weight cut off of $10^4$ Dalton. The solution retained in this filtration is dialyzed and re-subjected to cation exchange column chromatography. The fractions absorbed to the column can be eluted with a gradient of increasing concentration of ammonium acetate. Fractions eluted that exhibit the highest enzyme activity are pooled and subjected to affinity column chromatography. Fractions from the affinity column that exhibit the highest enzyme activity are pooled and concentrated by ultrafiltration. The concentrated protein solution is then subject to gel filtration to thereby isolate Chlamysin B. The measurement of enzyme activity of the fractions obtained through the above mentioned isolation and purification processes can be performed by using killed *Micrococcus luteus* cells.

The Chlamysin B gene is derived by isolation of mRNA from the style of *Chlamys islandica* from which cDNA is then synthesized. Based on the amino acid sequences obtained from the purified Chlamysin B protein, degenerated oligonucleotides were custom made and utilized as primers in amplification of part of the Chlamysin B gene. The 290 bp PCR product of Chlamysin B was sequenced using the PCR primers as primers for sequencing. The sequence information serves as basis for the design of two intragenic oligonucleotides which were applied as primers using the previously described cDNA as templates. The resulting product of 490 bp and an additional poly A tail were sequenced and the cDNA and the cDNA sequence information used in the design of two new oligonucleotide primers that were used in PCR amplification of the entire Chlamysin B gene from cDNA or genomic DNA (isolated from the scallop muscle). The PCR products were cloned in a plasmid vector and the final PCR products and the subsequently cloned products were sequenced. Based upon the cDNA sequence, the mature transcript of the Chlamysin B gene from *Chlamys islandica* contains 490 nucleotides plus a tail of adenine ribonucleotides.

The following examples are intended to be illustrative of the present invention and to teach one of ordinary skill in the art to make and use the invention. These examples were not intended to limit the invention in any way.

EXAMPLE I

The novel protein, Chlamysin B, was isolated from the scallop waste of Arctic Scallop (*Chlamys islandica*) in accordance with the following procedure:

Thawed scallop viscera extract (30 liters) was added hydrochloric acid to a final pH of 4.8. The extract was left at room temperature (24° C.) for settling of the resulting floc. Four days later, the brown supernatant (15.6 liters) formed was recovered. The supernatant was then added 55 liters of 10 mM ammonium acetate buffer (pH 5.0) and placed in the cold room (6–8° C.). All further steps in isolation of Chlamysin B were carried out at 6–8° C.

The diluted supernatant (70.6 liters) was split into two portions, and applied in separate experiments to a S Sepharose FF column (11.3×10 cm) equilibrated with 10 mM ammonium acetate (pH 5.0). After washing the column with 9 liters of this buffer followed by 5.5 liters of 10 mM ammonium acetate buffer (pH 6.0), the absorbed fractions were eluted with 0.4 M ammonium acetate buffer (pH 6.0). The fractions containing enzyme activity in these two experiments were pooled. The flow rate during S Sepharose chromatography was 40 cm/hr.

The pooled fractions form the two S Sepharose experiments above were in separate experiment first ultrafiltered on an Amicon CH2 ultrafiltration unit fitted with an Amicon Hollow Fiber cartridge H1P 100-20. The filtration was performed with a mean flux of 75 liters/m$^2$/h and an operating pressure of 110×10$^3$ Pa. The permeate obtained in these experiments were combined and subsequently ultrafiltered using a Amicon Hollow Fiber cartridge H1P 10-43 at a mean flux of 30 liters/m$^2$/h. The retentate obtained by this ultrafiltration was further concentrated on a PM 10 ultrafilter using an Amicon Diaflo stirred cell. The solution (40 ml) retained in this filtration, was centrifuged (14000×g for 20 minutes) and dialyzed twice against 10 mM ammonium acetate buffer (pH 5.0).

Then this dialyzed protein solution was re-subjected to Sepharose FF column (1.6×10 cm) chromatography. After applying the sample, the gel was washed with 20 mM ammonium acetate buffer (pH 5.0) and the absorbed proteins was eluted by stepwise increasing the concentration of ammonium acetate. The major peak of enzyme activity eluting at 0.5 M ammonium acetate was collected. This protein solution was dialyzed against 10 mM ammonium acetate buffer (pH 6.0) and applied to a Blue Sepharose CL-6B column (1.6×13 cm) equilibrated with this buffer. The peak of enzyme activity eluted with 0.18 M ammonium acetate was collected. The proteins in this eluate were concentrated by ultrafiltration. The resultant solution was gel filtrated on a Sephacryl S 200 HR column (2.6×93 cm) equilibrated with 0.1 M ammonium acetate buffer pH 5.0. The eluted fractions containing enzyme activity was collected. An aliquot from each fraction was subjected to sodium dodecyl sulfate polyacrylamide gel electrophoresis (SDS PAGE) using the Phast System (Amersham Pharmacia Biotech) with precast PhastGel Homogeneous High Density gels. Pharmacia Peptide Marker Kit ($M_r$ range 2512–16949 Dalton) was used as marker peptides, and the gels were silver stained as described by W. Ansorge (1983) in *Electrophoresis* '82, pp 235–242. The fractions showing a single protein band of ~10 kDa in SDS PAGE were pooled and the protein was concentrated by ultrafiltration using a YM2 membrane disc.

By the above mentioned procedure, 1.45 mg of Chlamysin B was obtained from 30 liters of scallop viscera extract. The quantity of the protein was measured using the Bio-Rad Protein assay according to Bradford (1976) *Anal. Biochem.*, 72, pp 248–254. The purity of the Chlamysin B preparation was checked by SDS PAGE using NOVEX NuPAGE 10% Bis-Tris Gel with MES SDS running buffer according to NuPAGE electrophoresis protocols. The gel was stained with Coomassie G-250 using NOVEX Colloidal Blue Stain kit. As a result, a single stained band was obtained.

Amino acid analysis sequence of the Chlamysin B protein was performed by compositional analysis after vacuum hydrolysis. The hydrolysates were analyzed on an automatic amino acid analyzer Model 421 (Applied Biosystems).

The following results were obtained:

| Amino Acid | No. Moles/Mole Chlamysin B |
| --- | --- |
| Asp + Asn | 8.5 |
| Glu + Gln | 9.9 |
| Ser | 10.2 |
| Gly | 13.0 |
| His | 7.3 |
| Arg | 4.5 |
| Thr | 6.8 |
| Ala | 5.9 |
| Pro | 3.8 |
| Tyr | 3.5 |
| Val | 2.7 |
| Met | 1.0 |
| Cys | 11.5 |
| Ile | 3.0 |
| Leu | 4.3 |
| Phe | 2.2 |
| Lys | 4.4 |

The N-terminal amino acid sequences of Chlamysin B was analyzed by automatic Edman degradation using a protein sequencer Model 477A (Applied Biosystems) and a HP G 1005A sequenching system. As a result, a preliminary 30 amino acid sequence was obtained.

To determine the amino acid sequences of the peptide fragments from cyanogen bromide cleavage, Chlamysin B was reduced and alkylated with 4-vinyl pyridine (Fridman, M. Nilsen, R., Cornwell III, G. G., Husby, G. & Sletten, K. (1970) *J. Biol. Chem.*, 245, pp 3868–3871. Cyanogen bromide cleavage was performed on the reduced and alkylated Chlamysin B and the resulting polypeptides were separated by reverse phase HPLC using a Pep-S C2/C18 column (Amersham Pharamacia Biotech) as described by Foss, G. S., Nilsen, R. & Sletten, K. (1988) *Scand. J. Immunol.*, 47, pp 348–354. Peaks were collected and taken for Edman degradation. As a result, the amino acid sequences shown in SEQUENCES No:1 and 2 were obtained. Sequence No. 1 was in agreement with the preliminary N-terminal sequence. In Sequence No. 2, no additional amino acids were detected after the last glutamic acid, indicating that the C-terminal was reached.

The sequences are written left to right in the direction from the amino to the carboxyl terminus in accordance with standard nomenclature, amino acid residue sequences are denominated by a single letter code as indicated below.

| Amino Acid Residue | 3-Letter Code | 1-Letter Code |
| --- | --- | --- |
| Alanine | Ala | A |
| Arginine | Arg | R |
| Aspargine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

SEQUENCE LISTING

SEQUENCE No. 1

Sequence characteristics a) length: 25 amino acids b) type: amino acid c) Molecule type: peptide Sequence description.

```
1               5                   10
Ala His Asn Phe Ala Thr Gly Ile Val Pro Gln Ala/Ser 15                      25
Cys Leu Glu Cys Ile Cys Lys Thr Glu Ser

25
Gly Cys Arg
```

SEQUENCE No. 2

Sequence characteristics a) length: 29 amino acids b) type: amino acid c) Molecule type: peptide Sequence description.

```
1               5                   10              15
Met Ser Arg Tyr Ile Gly His Thr Ser Cys Ser Arg Thr Cys Glu 20                  25
Ser Tyr Ala Arg Leu His Asn Gly Gly Pro Pro Gly Cys Glu
```

EXAMPLE II

Antibacterial Activity Test:

The antibacterial activity of Chlamysin B obtained in Example II was tested against various Gram-positive and Gram-negative bacteria. Testing for antibacterial activity was based on the classical microtiter broth dilution method recommended by the National Committee of Laboratory Safety and Standards (NCLSS) as described by D. Amersterdam (1996) in "Antibiotics in Laboratory Medicine", Fourth Edition, pp 52–111.

Bacteria and Test Conditions:

| Bacteria | Medium* | Temperature | pH |
| --- | --- | --- | --- |
| Vibrio salmonicida NCIMB 2245 | MB | 12° C. | 6.2 |
| Escherichia coli ATCC 25922 | TSB | Room temp | 6.2–5.7 |
| Pseudomonas aeruginosa ATCC 27853 | TSB | Room temp | 6.2–5.7 |
| Proteus mirabilis ATCC 35659 | TSB | Room temp | 6.2–5.7 |
| Listeria monocytogeneses CCMG 1452 | TSB | 12° C. | 6.2–5.7 |
| Bacillus cereus ATCC 10987 | BHI | Room temp | 6.2 |
| Staphylococcus epidermidis ATCC 12228 | TSB | Room temp | 6.2–5.7 |
| Enterococcus faecalis ATCC 29212 | TSB | Room temp | 6.2–5.7 |

*Tryptic soy broth medium (TSB), brain heart infusion medium (BHI) and marine broth medium (MB) were from Difco. These media were dissolved in 0.1 M sodium phosphate buffer.

Method for Testing the Antibacterial Activity:

Broth assays were performed in sterile 96-well round bottom Costar 3790 polypropylene microtiter plates (Corning Costar Corporation). Serial doubling dilutions of Chlamysin B were made in 0.01% acetic acid (pro analysis grade, Merck), 0.2% bovine serum albumin (Cat. No. A-7511, Sigma). The concentration of Chlamysin B in test samples was from 250 μg/ml to 1.95 μg/ml. Overnight bacteria cultures in media were diluted to give $10^3$–$10^6$ colony forming units/ml. 100 μl bacterial suspension was added each well and 11 μl of test sample at varied concentrations was added and incubated at 12° C. or room temperature for 24–48 hours. An Ika-Vibra-VXR electronic mixing device (Janke & Kenkel) performed mixing of the cultures upon incubation. After the incubation, the degree of cell proliferation was examined by measuring the absorbance at 620 nm using a SPECTRAmax Plus Microplate Spectrophotometer (Molecular Devices). The minimal inhibitory concentration (MIC) was defined as the lowest concentration for which no bacterial growth was optically detectable. Aliquots of wells corresponding to MIC were plated on nutrition agar and the number of colony-forming units (CFU) was determined after 48 hours incubation. The minimal bactericidal concentration (MBC) was the lowest concentration that totally suppressed colony formation.

The effect of Chlamysin B was tested against various bacteria. The table below summarizes the result of these experiments. Chlamysin B inhibits the growth of the fish pathogenic bacteria tested at low concentrations in culture (see figure below). Aliquots of wells corresponding to MIC values were plated on nutrition agar and the number of colony-forming units was determined after 48 hours incubation. The MIC and MBC values obtained were 0.6–1.25 μM and 1.25–2.5 μM, respectively.

Chlamysin B was less effective on the other bacteria tested, see table below. At a concentration of 2.5 μM in culture, Chlamysin B inhibits the growth of L. monocytogeneses after 96-hours incubation, B. cereus, S. epidermidis and E. faecalis all after 24 hours incubation. Chlamysin B at this concentration in culture had no effect on the growth of the other bacteria tested. Increasing the concentration of Chlamysin B to 10 μM in culture at pH 5.7 resulted in complete inhibition of growth of E. Coli, P. aeruginose, P. mirabilis, S. epidermidis and E. faecalis after 24 hours incubation. In these experiments, overnight cultures of bacteria diluted $10^4$ fold before the bacterial suspension was used in assay. The delta absorbance at 620 nm in control wells after 24 hours incubation was 0.25–0.4 in these experiments. This gives a MIC value for Chlamysin B on these bacteria of ~10 µM.

These results show that Chlamysin B has antibacterial effect against Gram-positive and Gram-negative bacteria including fish pathogenic bacteria, bacteria that causes deterioration of food and bacteria which causes infections in humans.

The Effect of Chlamysin B on Bacteria:

| Bacteria | Chlamysin B 2.5 µM | 10 µM |
|---|---|---|
| *Vibrio salmonicida* NCIMB 2245 | Bacteria killed | Not tested |
| *Escherichia coli* ATCC 25922 | No inhibition of growth | Complete inhibition of growth |
| *Pseudomonoas aeruginoso* ATCC 27853 | No inhibition of growth | Complete inhibition of growth |
| *Proteus mirabilis* ATCC 35659 | No inhibition of growth | Complete inhibition of growth |
| *Listeria monocytogeneses* CCMG 1452 | ~50% inhibition of growth | Not tested |
| *Bacillus cereus* ATCC 10987 | ~80% inhibition of growth | Not tested |
| *Staphylococcus epidermidis* ATCC 12228 | ~80% inhibition of growth | Complete inhibition of growth |
| *Enterococcus faecalis* ATCC 29212 | ~10% inhibition of growth | Complete inhibition of growth |

SDS-PAGE electrophoresis and amino acid sequenching of the purified Chlamysin B protein indicated a mature and active protein of approximately 100 amino acids starting with serine or alanine (corresponding to position 18 in cDNA encoded product) and ending in a glutamic acid (corresponding to position 121 in the protein encoded by the cDNA). This suggests that the active (enzymatic and antibacterial) protein comprises 104 amino acids although no cleavage site is obvious for removal of the 16 amino acid in C-terminus of the protein. The putative 104 amino acid processing product is predicted to have MW=11402 Da, pI=6.70 and a net charge of minus 2.

The protein sequence of the potential Chlamysin B encoded by the cDNA is in full agreement with the amino acid sequence obtained from the active protein (one 25 residues N-terminal fragment and one 29 residues C-terminal fragment).

EXAMPLE III

Identification and Cloning of the Chalmysin B Gene mRNA Isolation, cDNA Synthesis and Chlamysin B Gene Amplification:

mRNA was isolated from the style of *Chlamys islandica* using the PolyATract System® 1000 (Promega) from which cDNA was synthesized by the use of Smart™ PCR cDNA Synthesis Kit (Clontech). Based on the amino acid sequences obtained from the purified Chlamysin B protein, degenerated oligonucleotides ChlaN4 and ChlaCT were custom made and utilized as primers in amplification of part of the Chlamysin B gene applying the Advantage® cDNA PCT Kit (Clontech). The 290 bp PCR product of Chlamysin B was sequenced following the instructions for the Thermo Sequenase™ Radiolabelled Terminator Cycle Sequenching Kit (Amersham), using the PCR primers as primers for sequencing. The sequence information was the basis for the design of two intragenic oligonucleotides. These oligonucleotides CmarF and CmarR were applied as primers in 3'- and 5'-RACE reactions, respectively, conducted according to the Marathon™ cDNA Amplification Kit (Clontech), using the previously described cDNA as template. The resulting 3'- and 5'-RACE products, representing a cDNA product of 490 bp and an additional polyA-tail, were sequenced and the cDNA sequence information of the 3'- and 5'-ends were included in the design of two new oligonucleotide primers ChlaBF and ChlaBR that were used in PCR amplification of the entire Chlamysin B gene from cDNA or genomic DNA (isolated from the muscle of one scallop), and the PCR products were cloned in a plasmid vector contained in the pCR-Scrip™ Amp SK(+) Cloning Kit (Stratagene). The final PCR products and the subsequently cloned products were sequenced and relevant computer-aided sequence analysis were performed.

Chlamysin B Gene Sequence, the Encoded Protein Sequence and Sequence Attributes:

The 490 nucleotide cDNA sequence and the polyA tail ($[a]_n$) and the encoded 137 amino acid protein product of Chlamysin B from *Chlamys islandica* SEQ Nos. 3–4. A predicated 17 residue signal peptide is written in italics and the 104 amino acid sequence of the expected mature active protein is highlighted. The C-terminal 16 residues are believed to be removed by unknown mechanisms. Nucleotide variations thought to represent allelic variations are shown in low-letter cases above the cDNA sequence, and the resulting amino acid variations are shown below the protein sequence. A strong consensus 3' polyadenylation signal is underlined, and a potential 5' ribosome binding site overlapping the start codon is underlined and highlighted.

```
                                               c                    a
  1 GCAGACCAGTAC GACATAATGA TGTATTTTGTTCTGTTTTGTTTGTTGGCAGCAGGGACG
                            M  M  Y  F  V  L  F  C  L  L  A  A  G  T
                                              L                 T cg                              c
 61 ACTTACGGGTCTCACAATTTTGCCACAGGAATTGTCCCACAGAGTTGTTTGGAGTGTATT
     T  Y  G  S  H  N  F  A  T  G  I  V  P  Q  S  C  L  E  C  I
              A                             H

121 TGTAAGACGGAGTCCGGATGTAGAGCTATTGGATGCAAATTTGACGTATACTCCGACTCG
     C  K  T  E  S  G  C  R  A  I  G  C  K  F  D  V  Y  S  D  S

181 TGTGGCTACTTTCAGTTAAAACAGGCCTACTGGGAGGACTGTGGCAGGCCAGGAGGATCT
     C  G  Y  F  Q  L  K  Q  A  Y  W  E  D  C  G  R  P  G  G  S t
241 CTCACTTCTTGTGCTGATGACATCCACTGTTCGTCCCAGTGTGTACAGCACTACATGAGC
     L  T  S  C  A  D  D  I  H  C  S  S  Q  C  V  Q  H  Y  M  S

301 AGATACATAGGCCATACTTCGTGTTCACGAACCTGTGAGAGCTATGCCCGGTTACACAAT
     R  Y  I  G  H  T  S  C  S  R  T  C  E  S  Y  A  R  L  H  N

361 GGTGGCCCACATGGTTGTGAACATGGCTCTACCTTAGGCTACTGGGGTCATGTACAGGGT
     G  G  P  H  G  C  E  H  G  S  T  L  G  Y  W  G  H  V  Q  G

421 CACGGCTGCTGAAGGTCGCAGTCATTATTGTTTTATATAAGGCTTT AATAAA ACACTAAA
     H  G  C  *

481 ATATTCATTC[a]ₙ
```

Based on the cDNA sequence, the mature transcript of the Chlamysin B gene from *Chlamys islandica* contains 490 nucleotides plus a tail of adenine ribonucleotides. An open reading frame of 411 nucleotides may code for a protein of 137 amino acids starting with two consecutive methionines. cDNA sequences and genomic sequences reveal alternative nucleotides in positions 36 (T or C), 52 (G or A), 69 (G or C), 70 (G or T), 102 (G or A), and 243 (C or T). These alternations found in cDNA as well as in genomic copies of the Chlamysin B gene suggest that *Chlamys islandica* carries allelic copies of the gene and similar amounts of transcripts are apparently formed from the alleles. The nucleotide variations produce the following amino acid variations; Phe or Leu in residue 7, Ala or Thr in residue 12, Ser or Ala in residue 18 and Gln or His in residue 28. Nucleotide variations 69 and 243 do not affect the amino acid coded for. The 137 amino acid protein, of which the 17 N-terminal residues are predicted to form a cleavable signal peptide regardless of the residue (serine or alanine) in position 18, has a predicted molecular weight (MW) of 14964 Da, the net charge is minus 2 and the calculated isoelectric point (pI) is 6.90.

Recombinant Production of Chlamysin B:

PCR was used to produce three different constructs of the Chlamysin B gene containing the coding parts for the entire gene Chlamysin B product including Signal peptide plus the Mature active protein plus the Carboxyterminal part (SMC), the mature active protein plus the carboxyterminal part (MC), or the mature active protein (M). The following oligonucleotides were used as primer pairs in these Chlamysin B constructions; Sig+Cnco for the SMC product, Mnde+Cbam for the MC product, and Mnde+Mbam for the M product. The custom made oligonucleotides were designed to include the appropriate restriction enzyme recognition sequences for subsequent restriction of the PCR products. The SMC-encoding DNA was cut with NcoI, and NdeI and BamHI in combination were used to cut both PCR products encoding MC or M. Simultaneously, the plasmid pET15b (Novagen) was restricted with the same enzymes and used as a vector for the processed PCR products after the ligations to the individual DNA constructs. Following transformation of *E. coli* cells and subsequent isolations of plasmids from cells selected by growth in the presence of ampicillin, recombinant plasmids of pET-15b carrying the inserts of SMC, MC or M were sequenced for verification of insert sequences and in-frame fusions to the vector-contained sequences encoding a 6-residue histidine tag and a thrombin cleavage site. SMC with a C-terminal fusion peptide, and MC and M with N-terminal peptide fusions are predicted to have the molecular mass of 19.8 kDa, 15.4 kDa and 13.6 kDa, respectively. Finally, the three confirmed recombinant constructions were introduced to *E. coli* AD494 (DE3) cells (Novagen) for expression of Chlamysin B products. After IPTG [1 mM] induction for two hours at 21° C., cells were harvested and extracts were subjected to SDS-PAGE electrophoresis, using a NuPage™ 10% Bis-Tris gel (Novex) and a MES buffer, followed by coomassie staining for examination of the presence of recombinant proteins. As seen in the following Table, the respective cell extracts display the presence of specific protein bands having apparent molecular masses of approximately 20 kDa for SMC, 16 kDA for MC, and 14 kDa for M. The molecular sizes of these specific proteins are in full agreement with the predicted values. Thus, all three forms of Chlamysin B were produced at high levels by the AD494 (DE3) cells. Also noteworthy is the presence of Chlamysin B forms MC and M in periplasma despite the lack of signal peptides in these constructs.

Recombinant Chlamysin B produced in *E. coli* AD494 (DE3) cells

Three different Chlamysin B gene constructs were produced by PCR and inserted into the pET-15b plasmid vector for heterologous expression in *E. coli* cells. The constructs for the coding sequences, their vector-based fusion partners and the enzyme restriction sites for inserting in the vector is illustrated in A). The SDS-PAGE analysis after staining proteins in the gel is presented in B), representing proteins from periplasma in lanes 2–5 and cellular proteins in lanes 6–9 of SMC (3 and 7), MC (4 and 8) and M (5 and 9) together with the vector-containing control cells (2 and 6). In lane 1 is the Novex Mark 12 molecular size marker.

A)

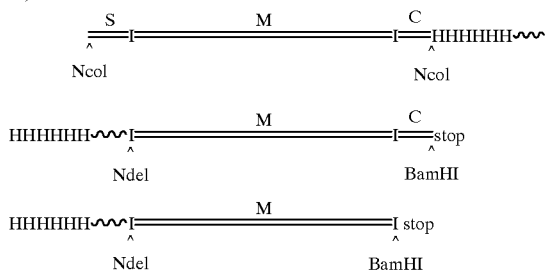

Oligonucleotide Primers Used for Cloning:

Underlined sequences are non-Chlamysin B sequences added to the oligonucleotide to provide restriction enzyme sites, translation stop signals, or the in-frame fusions to the vector-encoded fusion peptides SEQ Nos. 5–15.

```
Primer ChlaN4:     5'- GTWCCAGGMGCYTAYYTVGA -3'
Primer ChlaCT:     5'- CCDGGGGSCCSCCATTRTG -3'
Primer CmarF:      5'- TTGACGTATACTCCGACTCGTGTGG -3'
Primer CmarR:      5'- AGGTTCGTGAACACGAAGTATGGCC -3'
Primer ChlaBF:     5'- GCAGACCAGTACGACATAATGATG -3'
Primer ChlaBR:     5'- TATAAAACAATAATGACTGCGACCTTC -3'
Primer Sig:        5'- TACGTCCATGGGGATGTATTTTGTTCTGTTTTG -3'
Primer Cnco:       5'- TAGCTCCATGGCGCAGCCGTGACCCTGTAC -3'
Primer Mnde:       5'- TTAGCTCATATGKCTCACAATTTTGCCACA -3'
Primer Mbam:       5'- TAGCTGGATCCTATTCACAACCATGTGGGCC -3'
Primer Cbam:       5'- TAGCTGGATCCTAGCAGCCGTGACCCTGTAC -3'
Nucleotide symbols: A = Adenine
                    C = Cytosine
                    G = Guanine
                    T = Thymine
                    D = A + G + T
                    M = A + C
                    R = A + G
                    S = C + G
                    V = A + C + G
                    W = A + T
                    Y = C + T
```

The specific examples herein disclosed are to be considered as being primarily illustrative. Various changes beyond those described will no doubt occur to those skilled in the art and such changes are to be understood as forming a part of this invention insofar as they fall within the spirit and scope of the appended claims.

---

That which is claimed is:

1. An isolated Chlamysin B antibacterial protein.

2. The protein of claim 1 obtained from the Icelandic scallop *Chlamys islandica*.

3. The Chlamysin B antibacterial protein of claim 1 having the N-terminal amino acid sequence

```
1                   5                   10
Ala His Asn Phe Ala Thr Gly Ile Val Pro Gln Ala/Ser
```

```
                15                          25
Cys Leu Glu Cys Ile Cys Lys Thr Glu Ser

25
Gly Cys Arg
``` and a C-terminal amino acid sequence

```
1               5                    10
Met Ser Arg Tyr Ile Gly His Thr Ser Cys Ser Arg 15                  20
Thr Cys Glu Ser Tyr Ala Arg Leu His Asn Gly Gly

25
Pro Pro Gly Cys Glu.
```

4. An isolated Chlamysin B gene isolated from the Icelandic scallop *Chlamys islandica*.

5. The Chlamysin B gene of claim 4 having the sequence of

```
                                   c
  1 GCAGACCAGTACGACATAATGATGTATTTT
                    M   M Y F
         c                  a
    GTTCTGTTTTGTTTGTTGGCAGCAGGGACG
    V L F C L L A A G   T
        L               T cg
 61 ACTTACGGGTCTCACAATTTTGCCACAGGA
    T Y G S H N F A T G
          A
                   c
    ATTGTCCCACAGAGTTGTTTGGAGTGTATT
    I V P Q S C L E C I
          H

121 TGTAAGACGGAGTCCGGATGTAGAGCTATT
    C K T E S G C R A I
    GGATGCAAATTTGACGTATACTCCGACTCG
    G S K F D V Y S D S

181 TGTGGCTACTTTCAGTTAAAACAGGCCTAC
    C G Y F Q L K Q A Y
    TGGGAGGACTGTGGCAGGCCAGGAGGATCT
    W E D C G R P G G S t
241 CTCACTTCTTGTGCTGATGACATCCACTGT
    L T S C A D D I H C
    TCGTCCCAGTGTGTACAGCACTACATGAGC
    S S Q C V Q H Y M S

301 AGATACATAGGCCATACTTCGTGTTCACGA
    R Y I G H T S C S R
    ACCTGTGAGAGCTATGCCCGGTTACACAAT
    T C E S Y A R L H N

361 GGTGGCCCACATGGTTGTGAACATGGCTCT
    G G P H G C E H G S
    ACCTTAGGCTACTGGGGTCATGTACAGGGT
    T L G Y W G H V Q G

421 CACGGCTGCTGAAGGTCGCAGTCATTATTG
    H G C *
    TTTTATATAAGGCTTTAATAAAACACTAAA

481 ATATTCATTC[a]ₙ(SEQ ID NO:3).
```

$[a]_n$

* * * * *

SEQUENCE LISTING

<160> NUMBER OF SEQ ID NOS: 15

<210> SEQ ID NO 1
<211> LENGTH: 25
<212> TYPE: PRT
<213> ORGANISM: Chlamys islandica
<220> FEATURE:
<221> NAME/KEY: MOD_RES
<222> LOCATION: (12)
<223> OTHER INFORMATION: Ala or Ser

<400> SEQUENCE: 1

Ala His Asn Phe Ala Thr Gly Ile Val Pro Gln Xaa Cys Leu Glu Cys
 1               5                  10                  15

Ile Cys Lys Thr Glu Ser Gly Cys Arg
            20                  25

<210> SEQ ID NO 2
<211> LENGTH: 29

-continued

```
<212> TYPE: PRT
<213> ORGANISM: Chlamys islandica

<400> SEQUENCE: 2

Met Ser Arg Tyr Ile Gly His Thr Ser Cys Ser Arg Thr Cys Glu Ser
 1               5                  10                  15

Tyr Ala Arg Leu His Asn Gly Gly Pro Pro Gly Cys Glu
            20                  25

<210> SEQ ID NO 3
<211> LENGTH: 490
<212> TYPE: DNA
<213> ORGANISM: Chlamys islandica
<220> FEATURE:
<221> NAME/KEY: CDS
<222> LOCATION: (19)..(429)

<400> SEQUENCE: 3
gcagaccagt acgacata atg atg tat ttt gtt ctg ttt tgt ttg ttg gca        51
                   Met Met Tyr Phe Val Leu Phe Cys Leu Leu Ala
                    1               5                  10 gca ggg acg act tac ggg tct cac aat ttt gcc aca gga att gtc cca        99
Ala Gly Thr Thr Tyr Gly Ser His Asn Phe Ala Thr Gly Ile Val Pro
            15                  20                  25 cag agt tgt ttg gag tgt att tgt aag acg gag tcc gga tgt aga gct      147
Gln Ser Cys Leu Glu Cys Ile Cys Lys Thr Glu Ser Gly Cys Arg Ala
        30                  35                  40 att gga tgc aaa ttt gac gta tac tcc gac tcg tgt ggc tac ttt cag      195
Ile Gly Cys Lys Phe Asp Val Tyr Ser Asp Ser Cys Gly Tyr Phe Gln
    45                  50                  55 tta aaa cag gcc tac tgg gag gac tgt ggc agg cca gga gga tct ctc      243
Leu Lys Gln Ala Tyr Trp Glu Asp Cys Gly Arg Pro Gly Gly Ser Leu
 60                  65                  70                  75 act tct tgt gct gat gac atc cac tgt tcg tcc cag tgt gta cag cac      291
Thr Ser Cys Ala Asp Asp Ile His Cys Ser Ser Gln Cys Val Gln His
                80                  85                  90 tac atg agc aga tac ata ggc cat act tcg tgt tca cga acc tgt gag      339
Tyr Met Ser Arg Tyr Ile Gly His Thr Ser Cys Ser Arg Thr Cys Glu
            95                 100                 105 agc tat gcc cgg tta cac aat ggt ggc cca cat ggt tgt gaa cat ggc      387
Ser Tyr Ala Arg Leu His Asn Gly Gly Pro His Gly Cys Glu His Gly
        110                 115                 120 tct acc tta ggc tac tgg ggt cat gta cag ggt cac ggc tgc              429
Ser Thr Leu Gly Tyr Trp Gly His Val Gln Gly His Gly Cys
    125                 130                 135 tgaaggtcgc agtcattatt gttttatata aggctttaat aaaacactaa aatattcatt    489
c                                                                    490

<210> SEQ ID NO 4
<211> LENGTH: 137
<212> TYPE: PRT
<213> ORGANISM: Chlamys islandica

<400> SEQUENCE: 4

Met Met Tyr Phe Val Leu Phe Cys Leu Leu Ala Ala Gly Thr Thr Tyr
 1               5                  10                  15

Gly Ser His Asn Phe Ala Thr Gly Ile Val Pro Gln Ser Cys Leu Glu
            20                  25                  30

Cys Ile Cys Lys Thr Glu Ser Gly Cys Arg Ala Ile Gly Cys Lys Phe
        35                  40                  45
```

```
Asp Val Tyr Ser Asp Ser Cys Gly Tyr Phe Gln Leu Lys Gln Ala Tyr
 50                  55                  60

Trp Glu Asp Cys Gly Arg Pro Gly Gly Ser Leu Thr Ser Cys Ala Asp
 65                  70                  75                  80

Asp Ile His Cys Ser Ser Gln Cys Val Gln His Tyr Met Ser Arg Tyr
                 85                  90                  95

Ile Gly His Thr Ser Cys Ser Arg Thr Cys Glu Ser Tyr Ala Arg Leu
                100                 105                 110

His Asn Gly Gly Pro His Gly Cys Glu His Gly Ser Thr Leu Gly Tyr
            115                 120                 125

Trp Gly His Val Gln Gly His Gly Cys
130                 135
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
gtwccaggmg cytayytvga                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
ccdgggggsc csccattrtg                                            20

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 7
ttgacgtata ctccgactcg tgtgg                                      25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
aggttcgtga acacgaagta tggcc                                      25

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
gcagaccagt acgacataat gatg                                       24

```
<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
tataaaacaa taatgactgc gaccttc                                   27

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 11
tacgtccatg gggatgtatt ttgttctgtt ttg                            33

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
tagctccatg gcgcagccgt gaccctgtac                                30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
ttagctcata tgkctcacaa ttttgccaca                                30

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 14
tagctggatc ctattcacaa ccatgtgggc c                              31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 15
tagctggatc ctagcagccg tgaccctgta c                              31
```